(12) United States Patent
Zhang et al.

(10) Patent No.: US 8,460,722 B2
(45) Date of Patent: *Jun. 11, 2013

(54) **USE OF *NOCARDIA RUBRA* CELL WALL SKELETON IN THE PREPARATION OF ANTI-HPV INFECTION MEDICAMENTS**

(75) Inventors: Ce Zhang, Shenyang (CN); Yi Zhang, Shenyang (CN); Xiaoming Hong, Shenyang (CN); Guoying Zhang, Shenyang (CN); Jian Zhao, Shenyang (CN)

(73) Assignee: Shenyang Sun Bell Com Bio-Pharmaceutical Co., Ltd, Shenyang (CN)

( * ) Notice: Subject to any disclaimer, the term of this patent is extended or adjusted under 35 U.S.C. 154(b) by 903 days.

This patent is subject to a terminal disclaimer.

(21) Appl. No.: 12/067,891

(22) PCT Filed: Nov. 23, 2005

(86) PCT No.: PCT/CN2005/001977
§ 371 (c)(1),
(2), (4) Date: Apr. 28, 2008

(87) PCT Pub. No.: WO2007/033533
PCT Pub. Date: Mar. 29, 2007

(65) Prior Publication Data
US 2009/0028973 A1    Jan. 29, 2009

(30) Foreign Application Priority Data

Sep. 23, 2005 (CN) .......................... 2005 1 0105533

(51) Int. Cl.
*A61K 35/66* (2006.01)
*A01N 63/00* (2006.01)

(52) U.S. Cl.
USPC .......................................... 424/780; 424/93.4

(58) Field of Classification Search
None
See application file for complete search history.

(56) References Cited

U.S. PATENT DOCUMENTS

| 5,422,103 | A | * | 6/1995 | Stern et al. | 424/78.06 |
| 2004/0208896 | A1 | | 10/2004 | Hayashi | |
| 2006/0127518 | A1 | * | 6/2006 | Zhang et al. | 424/780 |
| 2007/0269543 | A1 | | 11/2007 | Zhang et al. | |

FOREIGN PATENT DOCUMENTS

| CN | 1879661 | 12/2006 |
| WO | WO-2004/022093 | 3/2004 |
| WO | WO-2005/023277 | 3/2005 |
| WO | WO 2005023277 A1 * | 3/2005 |

OTHER PUBLICATIONS thefreedictionary.com. Retrieved from the internet. <http://www.thefreedictionary.com/embrocation>. Retrieved on Mar. 16, 2010.*
webmd.com. Retrieved from the internet. <http://www.webmd.com/sexual-conditions/hpv-genital-warts/hpv-treatment-is-there-hpv-cure>. Retrieved on Mar. 12, 2010.*
Inoue et al. Effect of *Nocardia rubra* Cell-Wall Skeleton Treatment on Tumor Formation in Two-Stage Chemical Carcinogenesis of Mouse Skin. Cancer Immunol Immunother. (1981) 11: 207-210.*
Ghosh et al. Transdermal and Topical Drug Delivery Systems. 1997. Informa Health Care. p. 7.*
Gustafsson et al. Treatment of Skin Papillomas With Topical a-Lactalbumin-Oleic Acid. The New England Journal of Medicine. Jun. 2004. pp. 2663-2672.*
Lowry et al. Prophylactic Human Papilloma Vaccines. The Journal of Clinical Investigation. vol. 116, No. 5. May 2006. pp. 1167-1173.*
Baseman et al. The Epidemiology of Human Papillomavirus Infection. Journal of Clinical Virology. 32S. 2005. pp. S16-S24.*
Zhang, Ce et al., U.S. Office Action mailed on Sep. 23, 2009, directed to related U.S. Appl. No. 11/750,529; 13 pages.
Zhang et al., U.S. Office Action mailed Jun. 22, 2010, directed to related U.S. Appl. No. 11/750,529; 10 pages.

* cited by examiner

*Primary Examiner* — Christopher R. Tate
*Assistant Examiner* — Deborah Davis
(74) *Attorney, Agent, or Firm* — Morrison & Foerster LLP

(57) ABSTRACT

The invention refers to use of *Nocardia Rubra* Cell Wall Skeleton, especially the new use of the same in the preparation of Anti-HPV medicaments.

8 Claims, No Drawings

USE OF *NOCARDIA RUBRA* CELL WALL SKELETON IN THE PREPARATION OF ANTI-HPV INFECTION MEDICAMENTS

FIELD OF THE INVENTION

The invention refers to the medical use of *Nocardia Rubra* Cell Wall Skeleton, especially the new use of the same in the preparation of medicaments against human papilloma virus (HPV).

BACKGROUND OF THE INVENTION

Human papilloma virus (HPV) is a kind of DNA virus only hosted in skin and mucous complex squamous epithelia, and has not been cultured successfully outside of body. HPV induces a lot of benign papillary tumor or verruca of skin and mucous, some of which have latent carcinogenicity.

Nowadays, 120 types of HPV have been identified. The virus can be classed as skin type and genital meatus type according to their infected epithelia part on the body. About 35 types of HPV among them can infect the female genital meatus and about 20 types among them are related with the tumor. According to the dangerous degrees caused by different HPV types, HPV can be divided into high dangerous type and low dangerous type, low dangerous type includes for example: HPV6, 11, 42, 43, 44, CP8304 and the like, which induce benign lesions such as condyloma in genital meatus including (cervical intra-epithelial neoplasia) CIN-I. High dangerous types of HPV include HPV16, 18, 31, 33, 35, 45, 51, 52, 56, 58, 59, 68 and the like, which induce CIN-II, CIN-III and cervical cancer, it is especially this case for HPV16 and 18.

HPV infection is one of the most common infectious diseases that is transmitted by sex, and is related with sex life. It is believed by the person skilled in the art that HPV infection is the main factor of cervical cancer. HPV infection badly destroys the health of people, even results in death.

New infected cases may be about 10%-15% every year, based on the women all over the world. HPV infection is very common in many countries. Rate of incidence among young women having frequent sex is the highest; the peak age of infection is 18-28 years old. For most of the women, infective period is short, usually with 8-10 months. But there is still 10%-15% among women over 35 years old has a tendency of continuing infection. These continuous infected women are the high dangerous people of developing further into cervical cancer.

According to a related report, HPV infected people are 630 million in the world every year. 20 million of them are in the States of America. In addition, there are more than 5.5 million people who are diagnosed as HPV infection in America every year, in which more than one million are presented as wart of genitalia. HPV infection is becoming a public health problem.

According to the statistics made by the WHO, mortality induced by cervical cancer is in the second place among the death induced by cancer and in some developing countries it even is in the first place. There are more than 0.5 million cases of cervical cancer occurring every year, and about 0.2 million people are dead of cervical cancer, with 80% of them being in the developing country. Cervical cancer occupies 24% of the female malignant tumor in the developing country and 7% in the developed country. In the 21st century, cervical cancer has become one of the severest diseases that destroy the health of women in the world.

According to an inadequate statistics, in China there are 138 thousand women who suffer from cervical cancer and about 50 thousand women who are dead of cervical cancer every year, which is 25% based on the total number of cases occurring all over the world. But what is afflictive to the doctors is that a lot of patients can only be diagnosed in the late period when the valuable early therapy period is missed because early screening methods is imperfective, and moreover, patients newly suffering from cervical cancer are younger.

Prevention and Treatment of HPV Infection

There is no special method to prevent this disease. Generally, cutting off the transmitting way according to HPV transmission type is effective.

Small marts induced by the HPV may subside spontaneously, so no treatment is needed.

However, it is necessary to make operation for treating condyloma acuminatum because of its large scale of damnification. This method, meanwhile, is usually with high relapse rate. Physical therapy like galvanocantery or laser therapy and the like may also be applied.

On one aspect, there is no effective method to cure HPV infection and no effective medicament to cure cervical cancer, but on the other aspect cervical cancer is the first one whose sepathology has been known, and whose screening method is flawless. So it is very possible to achieve early diagnosis and early treatment through general screening. Cervical cancer may be the first one to be cured by humankind.

Moreover, many countries mainly apply "vaccine" to prevent from and treat with cervical cancer. By using vaccine, especially by using special combinational immune vaccine to stimulate the strong immune reaction of body, it is possible to clean up HPV infection and cancer cells remained after operation.

Nowadays, vaccines used for treating or preventing HPV virus in the world include that:

1. Preventative vaccine is virus-like granule vaccine, used as the target antigen of HPV preventive vaccine, which is major capsid protein L1 and minor protein L2 of HPV. Since expression protein of L1 and L2 can self assemble to form virus-like granule which is similar with the natural virus granule in special structure and epitope without containing HPV DNA, Good immunity effects by carrying out lots of animal experiments have been obtained. Clinical trials I/II have been approved and the applicant plans to carry trials III/IV in Europe.

2. Vaccine with preventive and therapeutic activity is chimeric virus-like granule, which is E7 chimeric virus granule made by L1 capsid protein and E7 polypeptide, having preventing and therapeutic activity. The chimeric virus granule can not only stimulate the production of neutralizing antibody, but also induce stronger E7 special CTL reaction and anti-tumor activity in body. At present, one kind of chimeric virus granule vaccine including HPV16 type L1, L2 and E7 target antigen will be tested in the clinical phage Itrial 3. One kind of therapeutic vaccine is vaccinia carrier vaccine which is the most common virus carrier, used as vaccinia virus for killing human smallpox, and having long, large scale history of inoculation applied by human. A clinical trial I about Cervical Cancer therapy was carried out in England by using recombined vaccinia carrier vaccine and E6, E7 protein expressing HPV16 and HPV18. There is no any adverse effect is observed. In some patients being tested, special antibody can be detected, CTL reaction and cytokines, which are different from each other, and may be related with the phages of cancer. Disadvantage is inhibiting re-immunization.

4. Polypeptide vaccine is also a kind of therapeutic vaccine. In the researches about antigens, the epitope recognized by CTL is determined, which provides the chance for developing polypeptide vaccine. Therefore, it is possible to enhance the production of tumor special CTL by using HPV16 type E6 or E7 polypeptide to immune. The clinical experiment of using HPV polypeptide vaccine to resist HPV related tumor is in clinical trials I/II, and there is no obvious adverse effect is observed. Persons with different inheritance background should use different polypeptide vaccine matching with HLA.

5. DNA vaccine is also a kind of therapeutic vaccine. The function of DNA vaccine is leading expressing plasmid carrying purpose gene into the body, and causing special immune reaction by expressing antigen in vivo. At present, the gene of DNA vaccine for treating HPV is HPV 16 type E7 gene. This kind of vaccine working by muscular injection is in the clinical I/II phase test. The weak immunity activity and problem of safety of DNA vaccine in the body should be noted.

For the research on HPV vaccine in China, in the aspect of preventive vaccine, people have finished the construction of HPV16 type L1 and L1/L2 recombined bacilliform virus strain which has been expressed in insect cells; observation of the formation of virus granule under electric mirror; successful construction of recombined copy with L1/L2 expression and non-copy type poxvirus vaccine strain. In the aspect of therapeutic vaccine research, people have constructed the recombined copy type expressing HPV16 E6/E7 protein and non-copy type poxvirus vaccine strain.

In a word, treatment of HPV infection and cervical cancer with vaccine is desired, and is hopeful. But it will take a long time to be applied by clinical use. HPV causing the cervical disease includes a lot of types, but present study is only focused on HPV16 type. There still is some limitation in the use and inoculation is restricted by the age of patient. So it is desired to prepare better and safer medicament as well as better therapeutic method to cure the disease.

*Nocardia Rubra* Cell Wall Skeleton agent is a well-known medicament in the art. In the prior art it is used for anti-fungus treatment such as for treatment of infection caused by *Candida albicans*, or also used in treatment of cervical erosion and for anti-herpes simplex and anti-herpes zoster, and the like. But there is no any report about using it in the treatment of HPV infection.

SUMMARY OF THE INVENTION

The purpose of invention is to provide a kind of medicament comprising *Nocardia Rubra* Cell Wall Skeleton and pharmaceutically acceptable carrier for treating HPV infection. Specifically, the invention is to provide the use of *Nocardia Rubra* Cell Wall Skeleton in the preparation of medicaments against HPV infection.

Said medicaments against HPV infection comprise *Nocardia Rubra* Cell Wall Skeleton as active agent and pharmaceutically acceptable carriers.

The carriers include excipient, preferably dextran.

The medicaments of present invention are topical preparation including ointment, cream, plaster, gelatin, lotion, tincture, liniment, oil agent, cataplasm and aerosol. Lotion, tincture and liniment are preferable.

1 ml or 1 mg of the medicaments comprises 0.001-1 mg *Nocardia Rubra* Cell Wall Skeleton.

The pharmacological mechanism of the drug for treating HPV infection is scientific. It is not only aiming to the nosogenesis of virus, but also suitable for the immunoregulation character of *Nocardia Rubra* preparations. Therefore, the medicament has an activity of cleaning HPV infection.

Among the patients infected HPV, most of them can overcome the infection by self-immune ability over certain time. But there still are some patients who can not overcome the infection because of their self-immune ability and so they suffer from a long time infection of HPV which may further develop into serious disease. Obviously, weak or strong self-immune ability is the key factor. Or in other words, whether can a person regulate immune ability or not is the key to overcome HPV.

According to a research for many years, *Nocardia Rubra* Cell Wall Skeleton preparation is proved as a non-special immune adjustor that has especially an obvious enhanced immunity activity on the skin and mucosal system.

After *Nocardia Rubra* Cell Wall Skeleton preparation being applied on the lesion, it can active the immune system of a body rapidly and gather a great deal of macrophage and NK cells to the injured area, and furthermore to enhance the ability of macrophage and NK cells to kill and clean ailing cell. Moreover, the preparation can also induce the production of CTL and many cytokines which can specifically kill and clear cells infected by virus, as well as enhancing obviously the immunity ability of body fluid.

It is studied that effective activation of CTL plays a very important role in cleaning HPV infection and in curing the squamous epithelial injury caused by HPV infection.

The degeneration of CIN is positive related with the existence of anti-HPV 16 neutralized antibody which can inhibit copied HPV re-infecting cells, decrease virus loads and further to inhibit the development of damage caused by HPV related cervical lesion.

From some research reports, about 87% of cervical cancers occur in the transitional zone. The amount of Langerhans cells in HPV turn-to-negative patients is more than that in HPV positive patients. So the amount of Langerhans cells in transitional zone can affect the degree of HPV infection, while *Nocardia Rubra* Cell Wall Skeleton is good for the increment and activation of Langerhans cells.

Although *Nocardia Rubra* Cell Wall Skeleton has no activity of direct killing and cleaning virus by itself, its function of enhancing immunity to kill and clean virus is exact and scientific. The action mechanism induced by such an indirect immune regulation further show the safety of the medicament.

As the methods used in the invention, the effect of *Nocardia Rubra* Cell Wall Skeleton on HPV virus is determined.

It is known that the detection methods for HPV in this field are as follows in general:

1. Cytology Smear Detection

This method is also called Pap staining detection, or smearing detection, comprising collecting the secretion of cervix and smearing that on the glass, and observing under microscope to find the vacuole cells or keratinization cells, with the detectable rate being 70-76%.

2. Cytology Detection of Thinprep (TCT)

The method comprises using a special brush to collect sample from the cervix, and then separating the impurity from the sample by using cell preservation solution, forming ultra thin and clear smear so as to determine the HPV virus and the type thereof. This method is also called TCT with detectable rate being 70-95%.

3. Immunohistochemistry Detection

In the HPV immuned animal, people want to find the HPV antigen according to polyclonal antibody in the PAP method for virus protein to prove virus antigen. When HPV protein is positive, the weak positive reaction can be seen in the epithelial cells, and brown granule seen in vacuole cell nucleus means positive. But detection rate is as low as 40-60%, and the sensitivity is also low. We cannot determine the type.

4. Detection of HPV by DNA (1) Polymerase Chain Reaction PCR

Secretion from the cervix is obtained by using a scraper or cotton stick steeped with NS, and then the DNA of HPV is obtained after centrifugation and washing steps, PCR amplification and gel electrophoresis are followed to obtain a result which is compared with sample to make the diagnosis. Though this method is easy, it cannot be used for orientation without knowing the virus being died or not.

(2) DNA Hybridization PCK

This is HPV-DNA Hybridization, CP-14 immune hybridization method. More than 3 phosphor dots that are positive are observed under the 400* fluorescence microscope. Nucleic acid hybridization can be used to determine the sequence of HPV-DNA, and PCR can be used to determine the specific HPV-DNA amplification zone. But the method is complex, expensive and needs special equipments and condition.

The present invention applies *Nocardia Rubra* Cell Wall Skeleton preparation for treating HPV infection by means of external use, injection and epidermal injection. Different period of treatment is applied for different state of illness, and good result is obtained. After the primary experiment the medicament is effective to both highly dangerous and minor dangerous HPV infection.

As is approved, *Nocardia Rubra* Cell Wall Skeleton preparation can be used for treating effectively HPV infection, and further for preventing cervical cancer. The invention provides a new method for treating venereal disease induced by HPV virus, and brings hope for people suffering from cervical cancer.

The invention is based on the viewpoint that HPV infection is the key factor of inducing cervical cancer. A lot of experiments are carried by using *Nocardia Rubra* Cell Wall Skeleton preparation to resist HPV virus, and a series of treatment methods are concluded for anti-HPV infection with good effect, and so a new way of anti-HPV infection is obtained.

Advantages of using *Nocardia Rubra* Cell Wall Skeleton preparation for anti-HPV infection includes:

1. Good safety: there is no adverse effect being observed and uncomfortable feeling being reported during the treatment.
2. Good suitability: topical application is for topical illness so as to avoid general reaction in the body.
3. Strong pertinence: the lesion occurs on skin and mucosa, while the medicament is good immunopotentiator when it is applied on these areas, and so the medicament shows strong pertinence.
4. Non-specificity: good activity is observed by using present method to treat every type of HPV infection.
5. Good efficiency: effective rate of HPV infection is 72.7%, and curable rate is 45.5%.
6. Easy to be used and popularized: only disposable medical utensils are needed in the treatment.
7. To cure as early as possible: The method complies with the principle of cervical cancer treatment of early finding and early treating.
8. Prevention: Anti-HPV infection is the first thing to do, reflecting the principle that prevention is more important than treatment.

DETAILED DESCRIPTION OF THE INVENTION

Example

In the following examples, diagnosis of the patients with the methods taught above is done for determining HPV infection, and then commercial product of *Nocardia Rubra* Cell Wall Skeleton preparation called "Nikejar" is applied to the subject affected by HPV via ex-coating directly to the lesion, or injected into the injured part, or epidermally injected into the targeted portion, multiple parts injection with minor amount of preparation is also possible. "Nikejar" is *Nocardia Rubra* Cell Wall Skeleton agent or preparation (produced by Sun Bell Com pharmaceutical Co. Ltd.).

20 days of a synthetical treatment are taken as one treatment cycle. The women during the menstruation should not use the medicament. Generally, light grade infection may be cured after one treatment cycle; moderate grade infection may turn to be negative after two treatment cycles; severe grade of infection will be cured after three treatment cycles. For those that are very serious, operation in combination with the medicaments is needed also when necessary.

The clinical experiment about HPV infection is as follows: Subjects are HPV infected women in 26-46 years old who are suffering from low risk HPV infection or high risk HPV infection. The subjects or patients in this age period are all in high risk of being infected; it is especially difficult for those older than 30 years old to recover by themselves. The administration times and interval time for test group are a little different. Generally, the first administration is started when a menstruation finish, and the patient is reexamined once the second menstruation end. No sex life in the treatment is required, or if it is inevitably the sex partner should use condom. Control group is not treated any more other than observation and detection. 11 patients among the test group insist to the end of the treatment, and 5 cases among control group insist to the end. The result is:

Test Group:

(1) Among the 11 cases that used present medicament for treating HPV infection, wherein 5 cases turned to be negative, 3 cases decreased the type I infection, and 3 cases changed nothing.

(2) About 3 cases without any change in test group, the reason might be that infection was serious, application time was short, and administration times were less. If we continue using the medicament, the effect would be good.

(3) Statistics about test group:

Curable rate: 45.5%, affectivity: 72.7%, 7 types including HPV6, 11, 16, 31, 56, 58 and 59 turned to be negative. Patients who are in high danger were 5 cases with 71.4% based on total patients of the group; patients who are in low danger were 2 cases with 28.6% based on total patients of the group.

(4) The new virus found in the No. 003 case may be a new kind infection.

Control Group:

(1) As to control group, nothing had been done but observation and record.

(2) The detection method for control group was the same with that for test group.

(3) The age of the patients for control group was the same with that for test group, and also including some older patients.

(4) During treating period, HPV positive was not changed for 5 cases selected from control group.

The results of test about "Nikejar" for treating patients in test group and for treating patients in control group is shown respectively in table-1 and table-2.

TABLE 1

Pro-test results of "Nikejar" in the treatment of HPV infection in test group

| Number | Name | Age | HPV infection type | The application method | Therapy method | Times | Using period | 3-7 days after menstruation | After next menstruation |
|---|---|---|---|---|---|---|---|---|---|
| 001 | WLJU | 37 | 58 | External use in cervix | Every other day | 6 | 3/8-3/18 | Negative | Negative |
| 002 | CHNI | 45 | CP8304 | External use in cervix | Every other day | 6 | 3/16-4/3 | CP8304 | CP8304 |
| 003 | ZLYI | 26 | 66 | External use in cervix | Every other day | 10 | 3/16-3/26 | 66 | 66 |
| 004 | TXYA | 46 | 56 | External use in cervix | Every other day | 6 | 3/18-3/28 | Negative | Negative |
| 005 | QIXU | 41 | 66 | External use in cervix | Every other day | 6 | 3/18-4/9 | 66 | 66 |
| 006 | WAYA | 39 | 59/6 | External use in cervix | Continue | 24 | 4/20-5/13 | Negative | Negative |
| 007 | LIPI | 26 | 31/33/59 | External use in cervix | Continue | 14 | 4/20-5/3 | 31/33 | 31/33 |
| 008 | WYME | 44 | 11/CP8304 | External use in cervix | Continue | 22 | 4/20-5/11 | CP8304 | CP8304 |
| 009 | XFYI | 42 | 16 | Cervical injection | Continue | 20 | 7/10-8/12 | Negative | Negative |
| 010 | HDME | 43 | 31 | Cervical injection | Every other day | 6 | 7/19-8/16 | Negative | Negative |
| 011 | XYLI | 26 | 31/58(CIN-I) | Cervical injection | Every other day | 10 | 7/6-8/4 | 58 | 58 |

TABLE 2

Table-2 Pro-test results of "Nikejar" in the treatment of HPV infection in control group

| Number | Name | Age | HPV infection type | The time of observation | 3-7 days after menstruation | After next menstruation |
|---|---|---|---|---|---|---|
| 101 | ZHPP | 41 | 58 | 5/7-6/16 | 58 | 58 |
| 102 | ZHXY | 45 | 56 | 6/1-7/5 | 56 | 56 |
| 103 | WALI | 30 | 11 | 6/18-7/29 | 11 | 11 |
| 104 | LINA | 38 | 52 | 6/6-7/15 | 52 | 52 |
| 105 | GLXA | 27 | 6 | 7/1-8/3 | 6 | 6 |

What is claimed is:

1. A method of treating a patient infected with human papilloma virus (HPV) comprising administering to the patient a composition comprising a therapeutically effective amount of *Nocardia rubra* cell wall skeleton.

2. The method according to claim 1, wherein the composition further comprises one or more pharmaceutically acceptable carriers.

3. The method according to claim 2, wherein the carriers include an excipient.

4. The method according to claim 3, wherein the excipient is dextran.

5. The method according to claim 1, wherein the composition is formulated for topical use.

6. The method according to claim 5, wherein the composition is in a form selected from the group consisting of an ointment, cream, plaster, gelatin, lotion, tincture, liniment, oil agent, cataplasm, and aerosol.

7. The method according to claim 5, wherein the composition is in the form of a lotion or liniment.

8. The method according to claim 2, wherein 1 ml or 1 mg of the composition comprises 0.001-1 mg of the *Nocardia rubra* cell wall skeleton.

* * * * *